US009125606B2

(12) United States Patent
Verkruijsse et al.

(10) Patent No.: US 9,125,606 B2
(45) Date of Patent: Sep. 8, 2015

(54) DEVICE AND METHOD FOR DETERMINING THE BLOOD OXYGEN SATURATION OF A SUBJECT

(71) Applicant: Koninklijke Philips Electronics N.V., Eindhoven (NL)

(72) Inventors: Willem Verkruijsse, Veldhoven (NL); Marek Janusz Bartula, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/135,644

(22) Filed: Dec. 20, 2013

(65) Prior Publication Data

US 2014/0275880 A1 Sep. 18, 2014

Related U.S. Application Data

(60) Provisional application No. 61/778,580, filed on Mar. 13, 2013.

(30) Foreign Application Priority Data

Mar. 13, 2013 (EP) ..................................... 13158884

(51) Int. Cl.
*G06K 9/00* (2006.01)
*A61B 5/1455* (2006.01)
(Continued)

(52) U.S. Cl.
CPC ......... *A61B 5/14552* (2013.01); *A61B 5/02416* (2013.01); *A61B 5/14551* (2013.01); *G06T 7/0012* (2013.01)

(58) Field of Classification Search
None
See application file for complete search history.

(56) References Cited

U.S. PATENT DOCUMENTS

| 5,408,998 | A | 4/1995 | Mersch |
| 8,761,853 | B2 | 6/2014 | Thaveeprungsriporn et al. |

(Continued)

FOREIGN PATENT DOCUMENTS

| JP | 2006271815 A | 10/2006 |
| WO | 0239873 A2 | 5/2002 |
| WO | 2012099534 A2 | 7/2012 |

OTHER PUBLICATIONS

Klaessens, J. H. G. M., et al.; Non-invasive skin oxygenation imaging using a multi-spectral camera system: Effectiveness of various concentration algorithms applied on human skin; 2009; SPIE; vol. 7174; 717408-1-13.

(Continued)

*Primary Examiner* — Siamak Harandi

(57) ABSTRACT

A device for determining blood oxygen saturation of a subject comprises an interface for receiving a data stream derived from detected electromagnetic radiation emitted or reflected from one or more skin portions of the subject, said data stream comprising a data signal per skin pixel for a plurality of skin pixels of said one or more skin portions. An analyzer determines the change in blood oxygen saturation of said plurality of skin pixels based on the data signals of said plurality of skin pixels. A selector selects a group of skin pixels comprising either the skin pixels showing the fastest change in blood oxygen saturation or said plurality of skin pixels except for skin pixels showing the slowest change in blood oxygen saturation. A processor determines the blood oxygen saturation of the subject based on the data signals of the selected group of skin pixels.

16 Claims, 6 Drawing Sheets

(51) Int. Cl.
  *A61B 5/024* (2006.01)
  *G06T 7/00* (2006.01)

(56) References Cited

U.S. PATENT DOCUMENTS

2010/0166252 A1 7/2010 Ahmed et al.
2010/0185068 A1 7/2010 Park et al.

OTHER PUBLICATIONS

Verkruysse, W., et al.; Remote plethysmographic imaging using ambient light; 2008; Opt Express; 16(26) 21434-21445.
Wieringa, F. P., et al.; In Vitro Demonstration of an SpO2-Camera; 2007; Computers in Cardiology; 34:749-751.
Wieringa, F. P., et al.; Contactless Multiple Wavelength Photoplethysmographic Imaging: A First Step Toward "SpO2 Camera" Technology; 2005; Annuls of Biomedical Engineering; 33(8)1034-1041.

DEVICE AND METHOD FOR DETERMINING THE BLOOD OXYGEN SATURATION OF A SUBJECT

CROSS REFERENCE TO RELATED APPLICATIONS

This application claims the benefit of U.S. provisional application Ser. No. 61/778,580 filed Mar. 13, 2013 and EP provisional application serial no. 13158884.0 filed Mar. 13, 2013, both of which are incorporated herein by reference.

FIELD OF THE INVENTION

The present invention relates to a device and a method for determining the blood oxygen saturation of a subject. In particular, the present invention relates to an unobtrusive optical measurement approach which can be used for detecting the arterial blood oxygen saturation in an observed subject, such as a person or animal. In this context, optical measurement refers to photoplethysmography (PPG) and, more specifically, to pulse oximetry.

BACKGROUND OF THE INVENTION

Vital signs of a person, for example the heart rate (HR), the respiration rate (RR) or the blood oxygen saturation, serve as indicators of the current state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heart beat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission and reflectance correspondingly. Besides information about the heart rate, a PPG waveform can comprise information attributable to further physiological phenomena such as the respiration. By evaluating the transmissivity and/or reflectivity at different wavelengths (typically red and infrared), the blood oxygen saturation can be determined.

Conventional pulse oximeters for measuring the heart rate and the arterial blood oxygen saturation (also called SpO2) of a subject are attached to the skin of the subject, for instance to a finger tip, earlobe or forehead. Therefore, they are referred to as 'contact' PPG devices. A typical pulse oximeter comprises a red LED and an infrared LED as light sources and one photodiode for detecting light that has been transmitted through patient tissue. Commercially available pulse oximeters quickly switch between measurements at a red and an infrared wavelength and thereby measure the transmissivity of the same area or volume of tissue at two different wavelengths. This is referred to as time-division-multiplexing. The transmissivity over time at each wavelength gives the PPG waveforms for red and infrared wavelengths. Although contact PPG is regarded as a basically non-invasive technique, contact PPG measurement is often experienced as being unpleasant, since the pulse oximeter is directly attached to the subject and any cables limit the freedom to move.

In this context, it shall be noted that "blood oxygen saturation" often refers to the average blood or tissue oxygen saturation in many research and medical fields which is generally different from the arterial oxygen saturation or SpO2. Pulse oximeters generally do not measure tissue saturation, rather they measure the arterial oxygen saturation which is typically quite a bit higher than the average blood oxygen saturation (which also contains venous blood). SpO2 is the non-invasive equivalent of SaO2 where in the former 'p' refers to pulse and in the latter 'a' refers to arterial. When reference is made to "blood oxygen saturation" or SpO2 herein, generally the arterial blood oxygen saturation is meant.

Recently, non-contact, remote PPG devices for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications. However, remote PPG devices typically achieve a lower signal-to-noise ratio.

Verkruysse et al., "*Remote plethysmographic imaging using ambient light*", Optics Express, 16(26), 22 Dec. 2008, pp. 21434-21445 demonstrates that photoplethysmographic signals can be measured remotely using ambient light and a conventional consumer level video camera.

Wieringa, et al., "*Contactless Multiple Wavelength Photoplethysmographic Imaging: A First Step Toward "SpO2 Camera" Technology*," Ann. Biomed. Eng. 33, 1034-1041 (2005), discloses a remote PPG system for contactless imaging of arterial oxygen saturation in tissue based upon the measurement of plethysmographic signals at different wavelengths. The system comprises a monochrome CMOS-camera and a light source with LEDs of three different wavelengths. The camera sequentially acquires three movies of the subject at the three different wavelengths. The pulse rate can be determined from a movie at a single wavelength, whereas at least two movies at different wavelengths are required for determining the oxygen saturation. The measurements are performed in a darkroom, using only one wavelength at a time.

It is desired to use non-contact camera-based PPG devices in neonatal intensive care unit (NICU) applications. Premature infants, the typical patients in the NICU, have frequent hypoxic periods (i.e. low SpO2) that require immediate care. Physicians then look at the SpO2 value to see if their intervention is successful. A responsive and accurate SpO2 measurement therefore is critical.

SUMMARY OF THE INVENTION

It is an object of the present invention to provide a device and a method for responsively and accurately determining the blood oxygen saturation of a subject, e.g. a premature infant in an NICU, for instance lying in an incubator.

In a first aspect of the present invention a device for determining the blood oxygen saturation of a subject is presented, the device comprising:

an interface that receives a data stream derived from detected electromagnetic radiation emitted or reflected from one or more skin portions of the subject, said data stream comprising a data signal per skin pixel for a plurality of skin pixels of said one or more skin portions, a data signal representing the detected electromagnetic radiation emitted or reflected from the respective skin pixel over time, an analyzer that determines the change in blood oxygen saturation of said plurality of skin pixels based on the data signals of said plurality of skin pixels, a selector that selects a group of skin pixels comprising either the skin pixels showing the fastest change in blood oxygen saturation or said plurality of skin pixels except for skin pixels showing the slowest change in blood oxygen saturation, and a processor that determines the blood oxygen saturation of the subject based on the data signals of the selected group of skin pixels.

In a further aspect of the present invention a corresponding method for determining the blood oxygen saturation of a subject is presented, the method comprising:

receiving a data stream derived from detected electromagnetic radiation emitted or reflected from one or more skin portions of the subject, said data stream comprising a data signal per skin pixel for a plurality of skin pixels of said one or more skin portions, a data signal representing the detected electromagnetic radiation emitted or reflected from the respective skin pixel over time, determining the change in blood oxygen saturation of said plurality of skin pixels based on the data signals of said plurality of skin pixels, selecting a group of skin pixels comprising either the skin pixels showing the fastest change in blood oxygen saturation or said plurality of skin pixels except for skin pixels showing the slowest change in blood oxygen saturation, and determining the blood oxygen saturation of the subject based on the data signals of the selected group of skin pixels.

In yet further aspects of the present invention, there are provided a computer program which comprises program code means for causing a computer to perform the steps of the method when said computer program is carried out on a computer as well as a non-transitory computer-readable recording medium that stores therein a computer program product, which, when executed by a computer processor, causes the method disclosed herein to be performed.

Preferred embodiments of the invention are defined in the dependent claims. It shall be understood that the claimed method, computer program and medium have similar and/or identical preferred embodiments as the claimed device and as defined in the dependent claims.

With the understanding that blood oxygen saturation is a systemic value (the oxygen saturation of arterial blood, pumped from the heart into the arterial system) rather than a value that is variable over the body, is has been concluded that during changes of arterial blood oxygenation, some body parts provide a blood oxygen saturation value that might differ from values at other body parts. For instance, during sudden drops of the blood oxygen saturation due to a health condition deterioration, pulse oximetry sensors on a peripheral of a body (e.g. finger oximeter) and a forehead sensor would show different blood oxygen saturation values. This is addressed in this disclosure by identifying areas that have delayed perfusion of (particularly arterial) blood and disregarding these areas, thus approaching the systemic blood oxygen saturation more responsively and accurately.

SpO2 is supposed to be a measure of the oxygen saturation of arterial blood. It is measured from the PPG signals caused by arterial pulsations. However, arterial blood arrives faster in some body parts than in other. Similarly, even on one body part, a hand for example, some skin areas are supplied earlier with arterial blood than others.

The remote PPG system known from the above cited disclosure of Wieringa aimed at imaging these differences rather than averaging them into one value. Other known non-contact PPG devices (e.g. a camera based PPG device) thus far average the obtained data signals (also called PPG signals) over a large skin area and thus find blood oxygen saturation values for skin with 'old' blood which may still have arterial blood that is not representative of that pumped out by the heart at that moment. The average blood oxygen saturation is thus an average of 'old' blood ('old' blood oxygen saturation) and new blood'. With the present invention those skin pixels or even skin regions are selected that are representative of the 'new blood' only, and thus the determined blood oxygen saturation is more representative of that.

In an embodiment said analyzer is configured to determine a blood oxygen saturation signal per skin pixel for said plurality of skin pixels and to determine the change in blood oxygen saturation of said plurality of skin pixels based on said blood oxygen saturation signals. Thus, from the data signal of a skin pixel a blood oxygen saturation signal is determined for said skin pixel, which is then preferably used in the subsequent process of selecting the optimum skin pixels and/or of determining the total blood oxygen saturation as proposed in a further embodiment according to which the processor is configured to determine the blood oxygen saturation of the subject from the blood oxygen saturation signals of the skin pixels of the selected group of skin pixels.

Said processor is further preferably configured to determine the blood oxygen saturation of the subject by averaging the blood oxygen saturation signals of the skin pixels of the selected group of skin pixels. In alternative embodiments it may also be possible to apply a kind of weighting to the blood oxygen saturation signals, e.g. taking into account the reliability and/or accuracy of them as e.g. determined by a quality index.

In an alternative embodiment said processor is configured to average the data signals of the skin pixels of the selected group of skin pixels to obtain an averaged data signal and to determine the blood oxygen saturation of the subject from the averaged data signal. This allows reducing a noise level of blood oxygen saturation measurement, while still differentiating areas with various dynamic of blood oxygen saturation changes.

There are various embodiments available for selecting the group of skin pixels. Generally, as defined above, the selected group of skin pixels comprises either the skin pixels showing the fastest change in blood oxygen saturation (i.e. a positive selection of skin pixels to use is made) or the selected group of skin pixels comprises all of said plurality of skin pixels except for skin pixels showing the slowest change in blood oxygen saturation (i.e. a negative selection of skin pixels to be excluded is made).

In an embodiment, said selector is configured to select said group of skin pixels by use of an upper and/or lower threshold for the blood oxygen saturation or by use of a threshold for the percentage of skin pixels of said plurality of skin pixels to be selected as said group. Said thresholds may be determined in advance, based on experimental data, but may also be adaptable, e.g. by the user, if it is noticed that the accuracy and/or reaction time of the determination of the blood oxygen saturation is insufficient. For instance, the lower thresholds can be set to a value in the range 80-95%.

In another embodiment said selector is configured to select all skin pixels of said plurality of skin pixels as said group if the change in blood oxygen saturation of said plurality of skin pixels is below a predetermined minimum threshold. This particularly holds in case of no substantial changes of the blood oxygen saturation.

In still another embodiment said selector is configured to select all skin pixels of said plurality of skin pixels as said group in the absence of a predetermined event, in particular in the absence of a hypoxic event.

For determining if such a predetermined event exists said interface is configured in an embodiment to receive an event indication signal indicating the presence and/or absence of said predetermined event. Said event signal may be generated by one or more external sensors, e.g. a sensor for recognizing a hypoxic event. One or more of such event sensors for sensing an event indication signal indicating the presence and/or absence of said predetermined event may also be included in the proposed device itself.

Alternatively or additionally, said analyzer is configured in an embodiment to determine if said predetermined event is absent or present based on one or more of said data signals, preferably acquired by said unobtrusive device of the present invention. Thus, the analyzer may recognize from an analysis of said data signals and, preferably, from blood oxygen saturation signals determined therefrom, that a predetermined event, e.g. a sudden drop and/or increase in the blood oxygen saturation for at least some of the pixels, appears.

Preferably, said data signals comprise at least two data signal components, wherein a first data signal component is representative of a first spectral portion, in particular a visible-light portion, and wherein a second data signal component is representative of a second indicative spectral portion, in particular an infrared portion. This idea makes use of the fact that a penetration depth of radiation which is dependent on blood absorption and tissue absorption is basically also dependent on the wavelength of incident radiation. Typically, infrared (or near-infrared) and red light penetrates deeper into the subject's tissue than light having shorter wavelengths. By way of example, the first spectral portion can be formed of a band or sub-band in the green portion of visible radiation.

In a preferred embodiment the proposed device further comprises an imaging unit, in particular a camera, that remotely detects electromagnetic radiation emitted or reflected from the subject, in particular in at least two different spectral ranges. The imaging unit is particularly suited for remote monitoring applications. The imaging unit can comprise one or more imaging elements. For instance, the imaging unit can comprise an array of photo sensors or charge-coupled devices. According to one embodiment, the imaging unit comprises at least two groups of imaging elements each of which is configured for detecting a single one of the data signal components. According to another embodiment, the imaging unit can make use of a single group of imaging elements having a response characteristic allowing for a detection of data signal components. The imaging unit can be further configured for capturing a sequence of image frames alternatingly representing the data signal components.

In another preferred embodiment the proposed device further comprises a radiation source, in particular a light source, that directs electromagnetic radiation to the subject, in particular in two or more different spectral ranges. The radiation source can be embodied by a broadband illumination source and/or can make use of a single group or two or even more groups of radiation elements. However, the proposed device does not necessarily have to comprise radiation source, but can also make use of ambient light sources which are not connected to the device.

In still another aspect of the present invention a device for determining blood oxygen saturation of a subject is presented, said device comprising a processing unit that is configured to receive a data stream derived from detected electromagnetic radiation emitted or reflected from one or more skin portions of the subject, said data stream comprising a data signal per skin pixel for a plurality of skin pixels of said one or more skin portions, a data signal representing the detected electromagnetic radiation emitted or reflected from the respective skin pixel over time, determine the change in blood oxygen saturation of said plurality of skin pixels based on the data signals of said plurality of skin pixels, select a group of skin pixels comprising either the skin pixels showing the fastest change in blood oxygen saturation or said plurality of skin pixels except for skin pixels showing the slowest change in blood oxygen saturation, and determine the blood oxygen saturation of the subject based on the data signals of the selected group of skin pixels.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
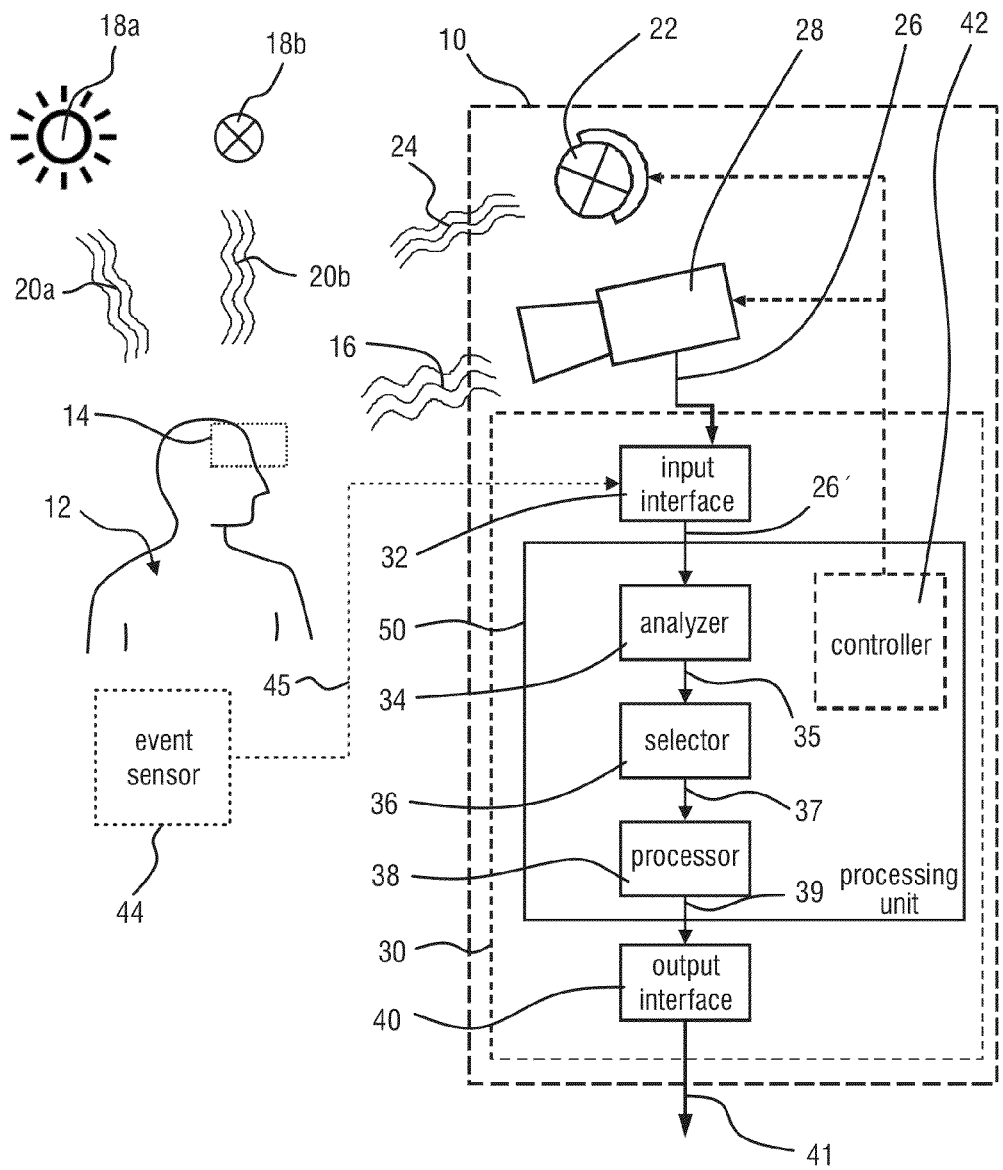
FIG. 1 shows a schematic diagram of a system in which a device according to the present invention is used.

FIG. 1 shows a schematic diagram of a system 10 in which a device 30 according to the present invention is used. The system 10 can be utilized for recording image frames representing a remote subject 12 or at least a portion 14 (a region of interest) of the subject 12 for remote PPG monitoring. The region of interest 14 comprises, by way of example, a forehead portion, a face portion or, more generally, one or more skin portions of the subject 12. The recorded data, for instance, a series of image frames, can be derived from electromagnetic radiation 16 reflected by the subject 12. Possibly, under certain conditions, at least part of the electromagnetic radiation could be emitted or transmitted by the subject 12 itself. Radiation transmission may occur when the subject 12 is exposed to strong illumination sources shining through the subject 12. Radiation emission may occur when infrared radiation caused by body heat is addressed and captured. However, for remote PPG applications, a huge portion of the electromagnetic radiation 16 to be captured can be considered radiation reflected by the subject 12. The subject 12 can be a human being or an animal, or, in general, a living being. Furthermore, the subject 12 can be considered a part of a human being highly indicative of a desired signal.

A source of radiation, such as sunlight 18a, an artificial radiation source 18b or a combination of several radiation sources, affects or impinges on the subject 12. The radiation sources 18a, 18b basically emit incident radiation 20a, 20b striking the subject 12. In addition, or in the alternative, the system 10 may also comprise or make use of an internal source 22 of electromagnetic radiation 24, which emits and directs incident radiation 24 to the subject 12 and which may also be part of the device 30 in an alternative embodiment. The internal source 22 of radiation 24 can be configured for directing radiation having defined characteristics to the subject 12, in particular radiation belonging to a defined spectral portion. Since in accordance with an embodiment of the invention, at least two distinct spectral portions are captured and processed, according to another aspect of this embodiment it is preferred that the internal source 22 of electromagnetic radiation 24 "matches" these spectral portions.

For extracting physiological information from the captured data, for instance, a sequence of image frames, radiation 16 from a defined part or portion of the subject 12, such as a the region of interest 14, is detected by an imaging unit 28. The imaging unit 28 can be embodied, by way of example, by an optical sensor means configured to capture information belonging to at least one spectral component of the electromagnetic radiation 16. In an embodiment, the imaging unit 28 is embodied by a camera or a set of cameras, such as a video camera (e.g. an RGB camera). The imaging unit 28 may also be part of the device 30 in an alternative embodiment.

Needless to say, the device 30 can also be adapted to process input signals, namely an input data stream 26, already recorded in advance and, in the meantime, stored or buffered. As indicated above, the electromagnetic radiation 16 can contain a continuous or discrete characteristic signal which can be highly indicative of at least one vital sign parameter 26, in the context of the present invention particularly the blood oxygen saturation.

An important field for PPG measurements is the determination of blood oxygen saturation (particularly arterial blood oxygen saturation). Contact pulse oximeters typically transmit red and infrared (or, more precisely, in some cases near infrared) light through a vascular tissue of the subject of interest. The respective light portions (R/IR) can be transmitted and detected in an alternating (fast-switching) manner. Given that the respective spectral portions are differently absorbed by oxygenated hemoglobin ($HbO_2$) and reduced hemoglobin (Hb), blood oxygen saturation eventually can be processed. An oxygen saturation ($SpO_2$) estimation algorithm can make use of a ratio of the signals related to the red and the infrared portion. Furthermore, the algorithm can consider a non-pulsatile signal component. Typically, the PPG signal comprises a DC component and a relatively small pulsatile AC component. Furthermore, SpO2 estimation generally involves an empirically derived calibration factor applied to the processed values. Typically, the calibration factor (or, calibration curve) is determined upon reference measurements involving invasive arterial blood oxygen saturation measurements (SaO2). One or more calibration factors are required since a PPG device basically detects a ratio of (spectral) signal portions which has to be transferred into a blood oxygen saturation value which typically involves a ratio of $HbO_2$ and Hb. For instance, but not intended to limit the present disclosure, blood oxygen saturation estimation can be based on the following general equation:

$$SpO2 = \frac{HbO_2}{HbO_2 + H_b}. \quad (1)$$

Generally, the characteristic signal is considered to contain a considerably constant (DC) portion and an alternating (AC) portion superimposing the DC portion. Applying signal processing measures, the AC portion can be extracted and, furthermore, compensated for disturbances. For instance, the AC portion of the characteristic signal can comprise a dominant frequency which can be highly indicative of the subject's 12 vascular activity, in particular the heart beat. Still, the characteristic signal, in particular the AC portion, can be indicative of further vital sign parameters. In this context, the detection of blood oxygen saturation is an important field of application. As indicated above, basically, blood oxygen saturation values can be computed taking into account the behavior of the AC portion of the characteristic signal at distinct spectral portions thereof. In other words, a degree of blood oxygen saturation can be reflected in different radiation absorbance at blood vessels. Furthermore, one can make use of the fact that the difference in absorbance due to the grade of oxygenation also varies significantly across different spectral portions. Typically, the DC component represents the overall light absorption of the tissue, venous blood, and arterial blood. By contrast, the AC component may represent the pulsatile arterial blood's absorption. Consequently, the determination of blood oxygen saturation ($S_pO_2$) can be expressed as:

$$SpO2 = C \cdot \frac{(AC/DC)_{red}}{(AC/DC)_{infrared}}, \quad (2)$$

where C is a calibration parameter. C may stand for a large variety of calibration parameters applicable to the AC/DC relationship and should therefore not be interpreted in the strict algebraic sense of equation (2). Typically, in prior art measurement devices, C represents a fixed constant value or a set of fixed constants.

The device 30 for determining blood oxygen saturation of a subject according to the present invention comprises an (input) interface 32 for receiving the data stream 26 (from the imaging unit 28 or from a storage unit or buffer) derived from detected electromagnetic radiation 16 emitted or reflected from one or more skin portions (region(s) or interest 14) of the subject 12. Said data stream 26 comprises a data signal per skin pixel for a plurality of skin pixels (preferably for all skin pixels) of said one or more skin portions 14, wherein a data signal represents the detected electromagnetic radiation 16 emitted or reflected from the respective skin pixel over time.

An analyzer 34 is provided for determining the change in blood oxygen saturation of said plurality of skin pixels (preferably for all skin pixels) based on the data signals 26' of said plurality of skin pixels received by said interface 32 and forwarded to the analyzer 34. Thus, corresponding change information 35 is output from the analyzer 34 indicating the change in blood oxygen saturation of said plurality of skin pixels.

Preferably, the analyzer computes relative amplitudes in the red and infrared spectral band from the temporal skin reflectance represented by the data signals of the plurality of the skin pixels.

The device 30 further comprises a selector 36 for selecting, based on the change information 35 from the analyzer, a group of skin pixels 37 comprising either (only) the skin pixels showing the fastest change in blood oxygen saturation or (only) comprising (all of) said plurality of skin pixels except for skin pixels showing the slowest change in blood oxygen saturation. Thus, at least in certain situations not the data signals of all skin pixels are selected but only the data signals of a smaller group of skin pixels 37 is selected.

A processor 38 is provided for determining the blood oxygen saturation 39 of the subject 12 based on the data signals of the selected group of skin pixels 37.

Finally, an (output) interface 40 can be provided to which the determined blood oxygen saturation 39 can be delivered, e.g. to provide output data 41 for further analysis and/or for display measures. Both interfaces 32, 40 can be embodied by the same (hardware) connectors.

In an embodiment a controller 42 is provided for selectively controlling at least one of the imaging unit 28 and the radiation source 22.

The analyzer 34, the selector 36 and the processor 38 (and, if provided, the controller 42) may be implemented by a common processing unit 50 which can be considered a computing device, or at least, part of a computing device driven by respective logic commands (program code) so as to provide for desired data processing. The processing unit 50 may comprise several components or units which are addressed in the following. It should be understood that each component or unit of the processing unit 50 can be implemented virtually or discretely. For instance, the processing unit 50 may comprise a number of processors, such as multi-core processors or single-core processors. At least one processor can be utilized by the processing unit 50. Each of the processors can be configured as a standard processor (e.g., central processing unit) or as a special purpose processor (e.g., graphics processor). Hence, the processing unit 50 can be suitably operated so as to distribute several tasks of data processing to adequate processors.

The processing unit 50 as well as the interfaces 32, 40 can be embodied in a common processing apparatus or housing, generally representing the proposed device 30. The imaging unit 28 and the radiation source 22 are generally external elements, but may also be integrated into the device 30, e.g. with a common housing with the other elements of the device 30.

Thus, according to a preferred embodiment of the present invention the blood oxygen saturation is generally evaluated for a plurality or all skin pixels that the imaging unit 28 (e.g. a camera) 'sees'. The skin pixels that have the fastest blood oxygen saturation recovery after/during periods in which blood oxygen saturation changes (e.g. a hypoxic event) are selected (e.g. through clustering methods) in the selector 36. The reported blood oxygen saturation is calculated from these skin pixels only, disregarding the pixels for skin area that have a slower dynamic of changes of oxygen saturation.

Preferably, all visible skin pixels are evaluated for their blood oxygen saturation value. The blood oxygen saturation values for all these pixels are analyzed for clustering at each moment in time. During a hypoxic event, for example, all skin pixels will have low blood oxygen saturation. All skin pixels will thus be in the same cluster and the reported (total) blood oxygen saturation is an average of all of these skin pixels. As soon as an intervention was successful, two clusters may start to form: one cluster (A) representing skin pixels with still 'old' arterial blood having a still low blood oxygen saturation, and another cluster (B) with 'fresh, new' blood having a (more accurate) higher blood oxygen saturation. In this case the reported (total) blood oxygen saturation is given as that of cluster B, i.e. only the cluster(s) is (are) used to compute the (total) blood oxygen saturation value comprising skin pixels from predominantly those skin areas that are perfused relatively early with arterial blood and thus are representative for the oxygen saturation of the arterial blood pumped out of the heart. This provides a faster and more accurate feedback, particularly after a hypoxic event.

For the selection of the skin pixels in such a situation an upper threshold for the blood oxygen saturation value may be used, i.e. only the data signals (or blood oxygen saturation signals) of skin pixels having blood oxygen saturation value above said upper threshold is used for determining the (total) blood oxygen saturation value.

In an alternative embodiment a threshold for the percentage of skin pixels from the total number of available skin pixels may be applied for this selection. For instance, a percentage of X % (X e.g. being in the range from 20 to 80) skin pixels having the highest blood oxygen saturation value may be selected for use in the determination of the (total) blood oxygen saturation value.

In a further alternative embodiment the monitoring system outputs two values of blood oxygen saturation measured from two subsets of pixels, thus providing the information about the dynamic of blood oxygen saturation changes The present invention may, however, not only be applied in case of a hypoxic event, but generally in case of other predetermined events as well. For instance, it may also be used to detect sudden or fast drops of the blood oxygen saturation. Also in such a situation some skin areas may quickly reflect such a sudden drop while other skin areas much slower reflect this drop. It might, however, be very essential to quickly recognize such a situation of a patient so that it is advantageous to use only skin portions that quickly reflect the drop of the blood oxygen saturation for determining the (total) blood oxygen saturation value.

In such a situation, for the selection of the skin pixels a lower threshold for the blood oxygen saturation value may be used, i.e. only the data signals (or blood oxygen saturation signals) of skin pixels having blood oxygen saturation value below said lower threshold is used for determining the (total) blood oxygen saturation value. In practice the lower threshold may be identical or different from the upper threshold. Further, also the threshold for the percentage of skin pixels may be used in such a situation similarly as explained above.

Generally, the selector 36 is configured to select all skin pixels of said plurality of skin pixels as said group of skin pixels for use in determining the total blood oxygen saturation value if the change in blood oxygen saturation of said plurality of skin pixels is below a predetermined minimum threshold, indicating situations without major changes of the blood oxygen saturation.

Preferably, the selector 36 is configured to select all skin pixels of said plurality of skin pixels as said group in the absence of a predetermined event, in particular in the absence of a hypoxic event. The interface 32 is preferably configured to receive an event indication signal 45 indicating the presence and/or absence of said predetermined event, for instance from an (optional) external event sensor 44 for sensing an event indication signal indicating the presence and/or absence of said predetermined event. Said event sensor 44 may also be part of the device 30 in an embodiment. Alternatively, the analyzer 34 is configured to determine if said predetermined event is absent or present based on one or more of said data signals. An event for possible changes of blood oxygen saturation can be detected by means of other vital body signs sensors, for instance respiratory or heart rate sensors (e.g. ECG or PPG).

Figure 2:
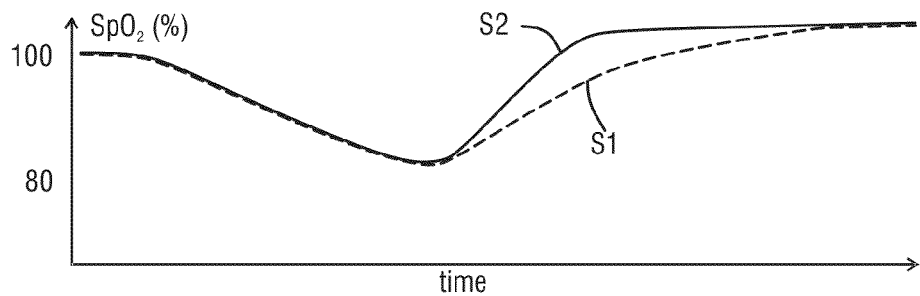
FIG. 2 shows a diagram illustrating the measured blood oxygen saturation with and without application of the proposed invention.

FIG. 2 shows a diagram illustrating two graphs showing the blood oxygen saturation value over time. The first graph S1 shows the blood oxygen saturation value over time as obtained by use of a convention method (i.e. generally taking all skin pixels into account). The second graph S2 shows the blood oxygen saturation value over time as obtained by use of the proposed method (i.e. generally disregarding certain skin pixels). It can be seen that during some times the graphs S1 and S2 are substantially identical, but that during the second graph S2 earlier and more accurately indicates a rise of the blood oxygen saturation value.

Figure 3A:
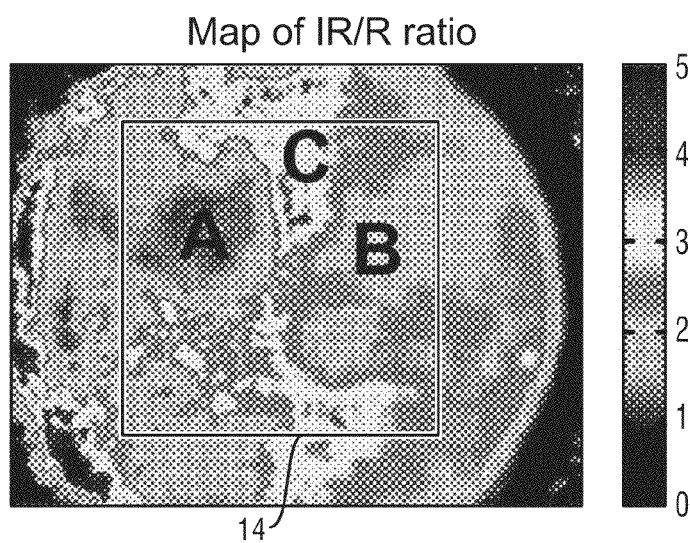
FIG. 3A shows a diagram illustrating the spatial distribution of blood oxygen saturation values within a region of interest.
Figure 3B:
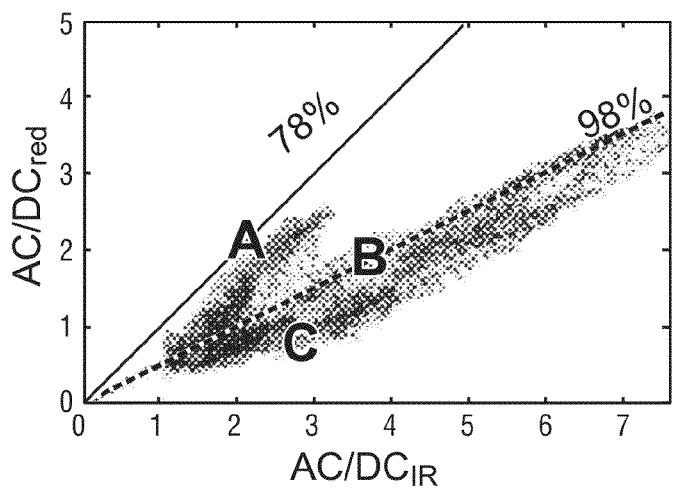
FIG. 3B shows a diagram illustrating red and IR signal amplitudes.
Figure 4A:
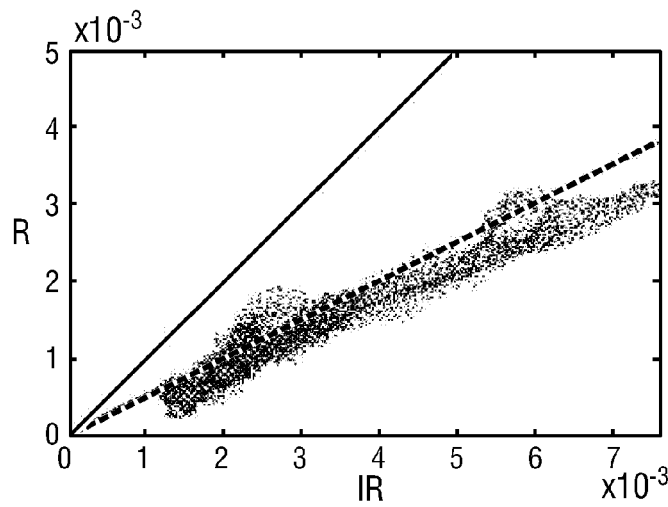
FIG. 4A shows a distribution of blood oxygen saturation signal values for a plurality of pixels before an experiment.
Figure 4B:
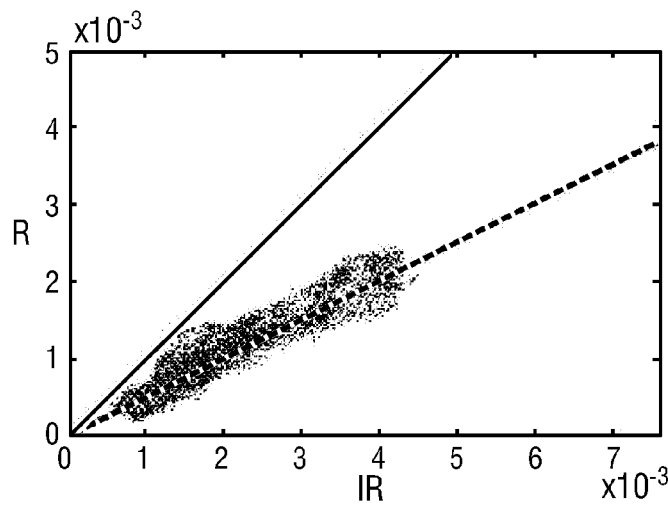
FIG. 4B shows a distribution of blood oxygen saturation signal values for a plurality of pixels while a subject is breath holding.
Figure 4C:
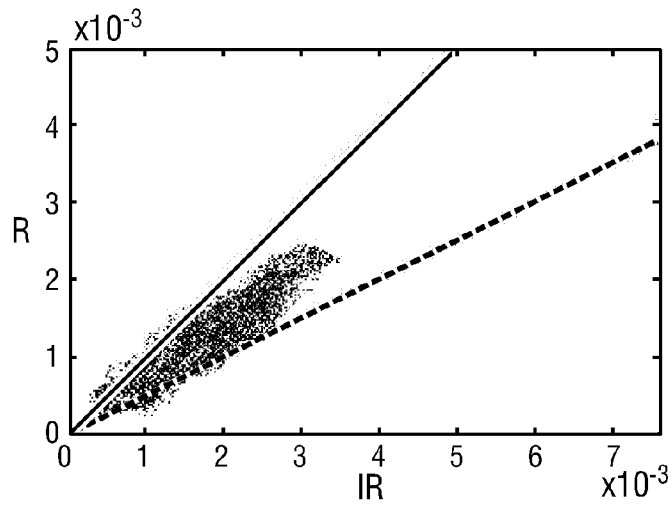
FIG. 4C shows a distribution of blood oxygen saturation signal values for a plurality of pixels while a subject is breath holding.
Figure 4D:
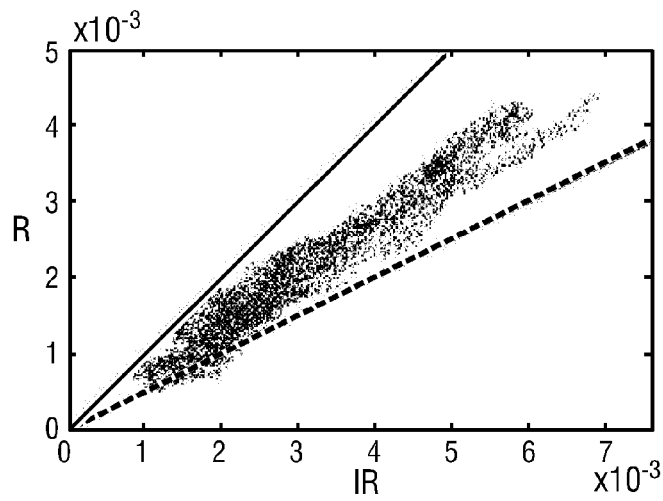
FIG. 4D shows a distribution of blood oxygen saturation signal values for a plurality of pixels while a subject is breath holding.
Figure 4E:
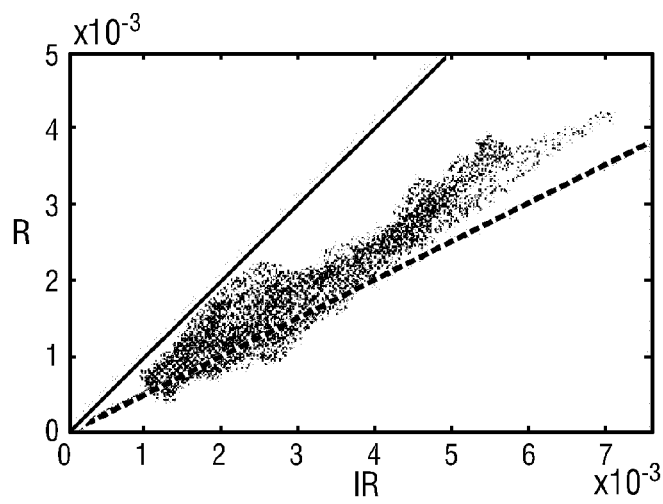
FIG. 4E shows a distribution of blood oxygen saturation signal values for a plurality of pixels while a subject is breathing.
Figure 4F:
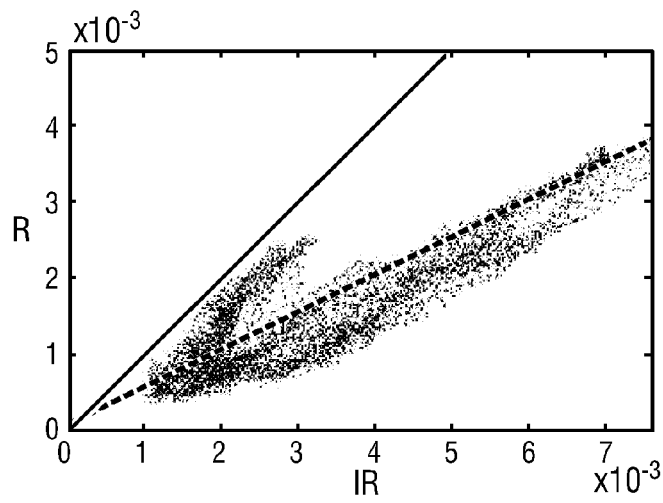
FIG. 4F shows a distribution of blood oxygen saturation signal values for a plurality of pixels while a subject is breathing.
Figure 4G:
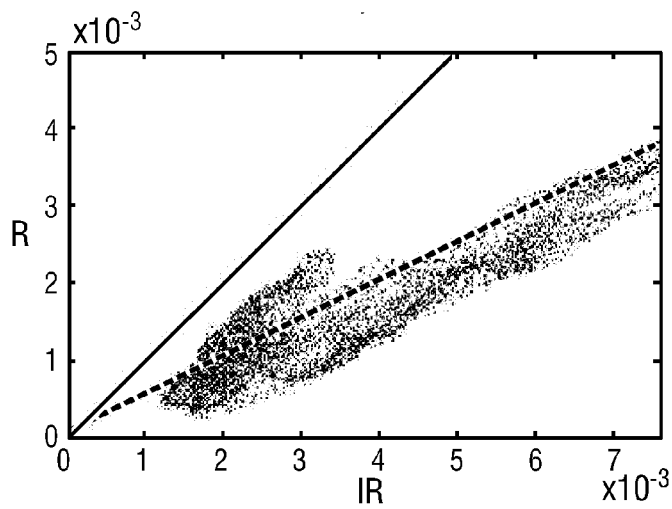
FIG. 4G shows a distribution of blood oxygen saturation signal values for a plurality of pixels while a subject is breathing.
Figure 4H:
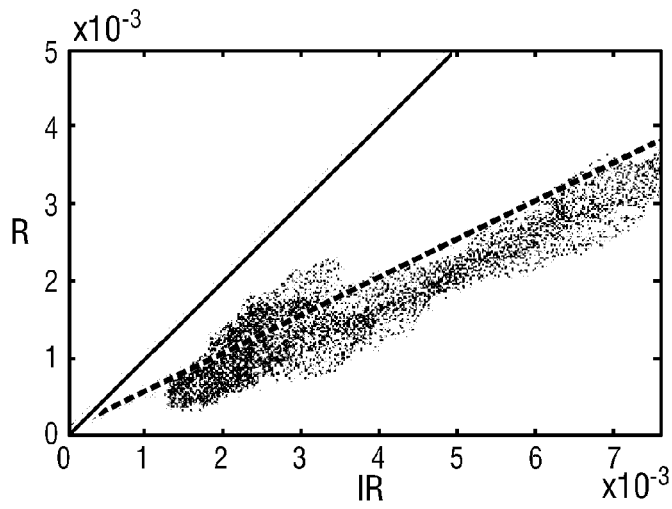
FIG. 4H shows a distribution of blood oxygen saturation signal values for a plurality of pixels while a subject is breathing.
Figure 4I:
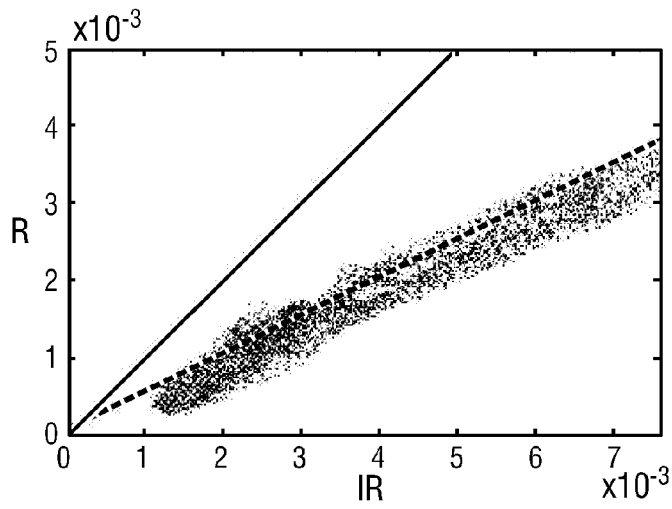
FIG. 4I shows a distribution of blood oxygen saturation signal values for a plurality of pixels in a normal state.

FIG. 3 shows diagrams illustrating the spatial distribution of blood oxygen saturation values. In particular, FIG. 3A shows a diagram illustrating, within a region of interest 14, for each skin pixel that ratio of red and IR data signal amplitude as indicated in equation (2). FIG. 3B shows a graph visually illustrating the red and IR signal amplitudes (here the straight lines with 78% and 98% represent blood oxygen saturation values; e.g. larger values for the ratio IR/red indicate high blood oxygen saturation values and vice versa). Three particular areas A, B, C are indicated in FIGS. 3A and 3B, wherein area A has the lowest blood oxygen saturation values and area 3 has the highest blood oxygen saturation values.

An experiment was performed. An individual was breathing normally for some time, then was holding his breath for approximately a minute to induce a drop in arterial blood oxygen saturation, a desaturation even, then was breathing normally again, causing a recovery of the blood oxygen saturation. Two cameras, one equipped with a red filter, another with an IR filter, were used to record the skin reflectance during these events. Data signal amplitudes were calculated for each of the skin pixels in the images (using a time window of approximately 10 seconds). The ratio of the red and IR data signal amplitudes is a measure for blood oxygen saturation. The results obtained over time are illustrated in the diagrams shown in FIG. 4 illustrating graphs of the same type as shown in FIG. 3B.

The graphs depicted in FIG. 4 show the chronological changes from the top left diagram to the bottom right diagram. FIG. 4A is obtained before the experiment. FIGS. 4B to 4D are obtained while holding the breath (leading to desaturation). FIGS. 4E to 4H are obtained while breathing again (leading to recovery). FIG. 4I shows the normal state again.

Figure 5:
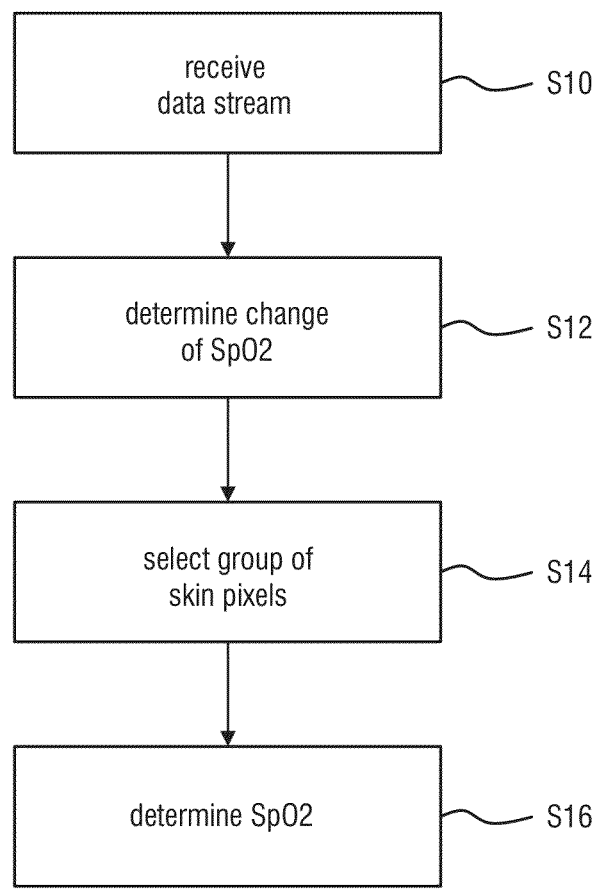
FIG. 5 shows a flowchart of a method according to the present invention.

FIG. 5 shows a flowchart of a method according to the present invention. In a first step S10 a data stream 26 is received that is derived from detected electromagnetic radiation 16 emitted or reflected from one or more skin portions of the subject 12, said data stream 26 comprising a data signal per skin pixel for a plurality of skin pixels of said one or more skin portions, a data signal representing the detected electromagnetic radiation 16 emitted or reflected from the respective skin pixel over time. In a second step S12 the change in blood oxygen saturation of said plurality of skin pixels is determined based on the data signals of said plurality of skin pixels. In a third step S14 a group of skin pixels is selected comprising either the skin pixels showing the fastest change in blood oxygen saturation or said plurality of skin pixels except for skin pixels showing the slowest change in blood oxygen saturation. In a fourth step S16 the blood oxygen saturation of the subject is determined based on the data signals of the selected group of skin pixels.

By way of example, the present invention can be applied in the field of health care, e.g. unobtrusive remote patient monitoring, general surveillances, security monitoring and so-called lifestyle environments, such as fitness equipment, or the like. Applications may include monitoring of oxygen saturation (pulse oximetry), heart rate, blood pressure, cardiac output, changes of blood perfusion, assessment of autonomic functions, and detection of peripheral vascular diseases.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

As used herein, the term "computer" stands for a large variety of processing devices. In other words, also mobile devices having a considerable computing capacity can be referred to as computing device, even though they provide less processing power resources than standard desktop computers. Furthermore, the term "computer" may also refer to a distributed computing device which may involve or make use of computing capacity provided in a cloud environment.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

The invention claimed is:

1. A device for determining blood oxygen saturation of a subject comprising:
   an interface configured to receive a data stream derived from detected electromagnetic radiation emitted or reflected from one or more skin portions of the subject, said data stream comprising a data signal per skin pixel for a plurality of skin pixels of said one or more skin portions, a data signal representing the detected electromagnetic radiation emitted or reflected from the respective skin pixel over time;
   an analyzer configured to determine a change in blood oxygen saturation of said plurality of skin pixels based on the data signals of said plurality of skin pixels;
   a selector configured to select a group of the skin pixels, the group including (a) the skin pixels showing a fastest change in blood oxygen saturation or (b) said plurality of skin pixels except for skin pixels showing a slowest change in blood oxygen saturation, said selector being configured to select said group of skin pixels by use of an upper or lower threshold for the blood oxygen saturation or by use of a threshold for a percentage of skin pixels of said plurality of skin pixels to be selected as said group; and
   a processor configured to determine the blood oxygen saturation of the subject based on the data signals of the selected group of skin pixels.

2. The device as claimed in claim 1,
   wherein said analyzer is configured to determine a blood oxygen saturation signal per skin pixel for said plurality of skin pixels and to determine the change in blood oxygen saturation of said plurality of skin pixels based on said blood oxygen saturation signals.

3. The device as claimed in claim 2,
   wherein said processor is configured to determine the blood oxygen saturation of the subject from the blood oxygen saturation signals of the skin pixels of the selected group of skin pixels.

4. The device as claimed in claim 3,
   wherein said processor is configured to determine the blood oxygen saturation of the subject by averaging the blood oxygen saturation signals of the skin pixels of the selected group of skin pixels.

5. The device as claimed in claim 1,
   wherein said processor is configured to average the data signals of the skin pixels of the selected group of skin pixels to obtain an averaged data signal and to determine the blood oxygen saturation of the subject from the averaged data signal.

6. The device as claimed in claim 1,
   wherein said selector is configured to select all skin pixels of said plurality of skin pixels as said group if a change in blood oxygen saturation of said plurality of skin pixels is below a predetermined minimum threshold.

7. The device as claimed in claim 1,
   wherein said data signals comprise at least two data signal components, wherein a first data signal component is representative of a first spectral portion, in particular a visible-light portion, and wherein a second data signal component is representative of a second indicative spectral portion, in particular an infrared portion.

8. The device as claimed in claim 1, further comprising at least one of the group consisting of:
   an imaging unit, in particular a camera, that remotely detects electromagnetic radiation emitted or reflected from the subject, in particular in two different spectral ranges, and
   a radiation source, in particular a light source, that directs electromagnetic radiation to the subject, in particular in two different spectral ranges.

9. A device for determining blood oxygen saturation of a subject comprising:
   an interface configured to receive a data stream derived from detected electromagnetic radiation emitted or reflected from one or more skin portions of the subject, said data stream comprising a data signal per skin pixel for a plurality of skin pixels of said one or more skin portions, a data signal representing the detected electromagnetic radiation emitted or reflected from the respective skin pixel over time;

an analyzer configured to determine a change in blood oxygen saturation of said plurality of skin pixels based on the data signals of said plurality of skin pixels;

a selector configured to select a group of the skin pixels, the group including (a) the skin pixels showing a fastest change in blood oxygen saturation or (b) said plurality of skin pixels except for skin pixels showing a slowest change in blood oxygen saturation, wherein said selector is configured to select all skin pixels of said plurality of skin pixels as said group in response to at least one of:
  absence of a hypoxic event; or
  a change in blood oxygen saturation of said plurality of skin pixels being below a predetermined minimum threshold; and a processor configured to determine the blood oxygen saturation of the subject based on the data signals of the selected group of skin pixels.

10. The device as claimed in claim 9,
wherein said interface is configured to receive an event indication signal indicating the presence or absence of said predetermined event.

11. The device as claimed in claim 9,
wherein said analyzer is configured to determine if said predetermined event is absent or present based on one or more of said data signals.

12. The device as claimed in claim 9,
further comprising an event sensor that senses an event indication signal indicating the presence or absence of said predetermined event.

13. A method for determining blood oxygen saturation of a subject comprising:
receiving a data stream derived from detected electromagnetic radiation emitted or reflected from one or more skin portions of the subject, said data stream comprising a data signal per skin pixel for a plurality of skin pixels of said one or more skin portions, a data signal representing the detected electromagnetic radiation emitted or reflected from the respective skin pixel over time, determining a blood oxygen saturation of each skin pixel of said plurality of skin pixels based on the data signals of said plurality of skin pixels, determining a rate of change in the determined blood oxygen saturation of each skin pixel, separating the plurality of skin pixels into a first group of skin pixels showing a faster rate of change in blood oxygen saturation and a second group of skin pixels showing a slower rate of change in blood oxygen saturation, and determining the blood oxygen saturation of the subject based on the data signals of the first group of skin pixels.

14. A computer readable non-transitory medium having instructions stored thereon which, when carried out on a computer, cause the computer to perform the steps of the method as claimed in claim 13.

15. A device for determining blood oxygen saturation of a subject comprising a computer processing unit that is programmed to:

receive a data stream derived from detected electromagnetic radiation emitted or reflected from one or more skin portions of the subject, said data stream representing detected electromagnetic radiation emitted or reflected from each skin pixel of a plurality of skin pixels over time, determine the change in blood oxygen saturation of each of said plurality of skin pixels, select a subset of the plurality of skin pixels, the subset including a fraction of the skin pixels showing a fastest change in blood oxygen saturation, and determine the blood oxygen saturation of the subject based on only the the selected subset of the plurality of skin pixels except under preselected physiological conditions, under the preselected physiological conditions calculating the blood oxygen saturation of the subject based on all of the plurality of skin pixels.

16. The device as claimed in claim 15, wherein the preselected physiological conditions include at least one of the change in the blood oxygen saturation being below a predetermined minimum or an absence of the predetermined event.

* * * * *